United States Patent [19]

Michelet et al.

[11] 4,263,462
[45] Apr. 21, 1981

[54] PROCESS FOR THE PREPARATION OF UNSATURATED ETHERS

[75] Inventors: Daniel Michelet, Tassin La Demi Lune; Michel Rakoutz, Oullins, both of France

[73] Assignee: Philagro, Lyons, France

[21] Appl. No.: 92,415

[22] Filed: Nov. 7, 1979

[30] Foreign Application Priority Data

Nov. 30, 1978 [FR] France ................. 78 34297

[51] Int. Cl.$^3$ ............................................. C07C 41/01
[52] U.S. Cl. ................................................. 568/652
[58] Field of Search ........................ 568/650, 652, 654

[56] References Cited
U.S. PATENT DOCUMENTS 2,378,698  6/1945  Gibbs .................................. 568/650
3,927,118 12/1975  Ozretich .

Primary Examiner—Bernard Helfin
Attorney, Agent, or Firm—Browdy and Neimark

[57] ABSTRACT

Unsaturated ethers of diphenols are prepared from alkenyl halides and diphenols as reagents and by carrying out the reaction in two zones at different temperatures.

Intermediates for perfumes, aromas and insecticides are so prepared.

27 Claims, No Drawings

PROCESS FOR THE PREPARATION OF UNSATURATED ETHERS

The present invention relates to a process for the preparation of unsaturated ethers of diphenols.

It is known to prepare unsaturated ethers of diphenols by reacting alkenyl halides with diphenols in the presence of alkaline agents (French Pat. No. 2,255,279).

One object of the present invention is to provide an improved process for the preparation of unsaturated ethers of diphenols.

Another object of the invention is to prepare $\beta,\gamma$-unsaturated alkenyloxyphenols from diphenols and alkenyl halides, with improved degrees of conversion and improved yields.

Another object of the invention is to prepare monoethers of diphenols preferentially, by preventing as much as possible the formation of diethers (0-alkylation side reaction) or of alkenyl diphenols (C-alkylation side reaction).

Another object of the invention is to provide a process for the preparation of alkenyloxyphenols, which makes it possible to use simple reagents, in particular alkali metal derivatives, as the basic agents.

It has now been found that these objects can be achieved by virtue of a new process which forms the subject of the present invention.

This process relates to the preparation of a $\beta,\gamma$-unsaturated alkenyloxyphenol from a diphenol and a $\beta,\gamma$-unsaturated alkenyl halide, wherein, in a first zone, there is a liquid medium consisting of two liquid phases of which one is organic and the other is aqueous, these phases being mixed with one another, and the liquid medium being obtained by mixing the diphenol, the $\beta,\gamma$-unsaturated alkenyl halide, an organic solvent, a basic agent, water and a quaternary ammonium or phosphonium derivative, the temperature of this first zone being such that substantially no chemical reaction of the alkenyl halide takes place, and wherein the organic phase is then separated from the aqueous phase and is heated in a second zone, this heating being effected at a temperature which is sufficient for the alkenyl halide to react.

That which essentially distinguishes the first zone from the second zone is that one (the second zone) is at a higher temperature than the other (the first zone). These two zones can be separate or together from the point of view of their location, but, according to a preferred embodiment, they are separate. In this case, the organic phase is extracted from the liquid medium in the first zone and is then transferred into the second zone.

According to a preferred variant of the invention, the liquid medium is recycled one or more times from the second zone into the first zone, it being possible for these recycling operations to be carried out either discontinuously or continuously. Thus, all or part of the liquid medium in the second zone can be reintroduced into the first zone; several successive treatments can thus be carried out alternately in the first zone and then in the second zone until there is enough alkenyloxyphenol in the second zone, at which point it is extracted and/or separated off by any means which is in itself known. When operating continuously under conditions of this type, part of the organic phase is then removed continuously from the second zone, this part is introduced into the first zone, part of the organic phase is extracted continuously from the first zone and this part is introduced into the second zone. In order to save energy, heat exchange is carried out between the liquid leaving the second zone and the liquid leaving the first zone, so as to maintain the high temperature in the second zone.

As the process of the invention proceeds, either continuously or discontinuously, it is of course possible to add constituents of the liquid media and/or reagents to the liquid media in the first zone and/or in the second zone. The diphenol and the alkenyl halide can thus be introduced either into the first zone or into the second zone; preferably, the basic agent is added to the first zone and, also preferably, there is no aqueous phase in the second zone.

It was indicated above that the liquid medium in the first zone was obtained by mixing the diphenol, the $\beta,\gamma$-unsaturated alkenyl halide, an organic solvent, a basic agent, water and a quaternary ammonium or phosphonium derivative; however, it must be clearly understood that these constituents are not necessarily introduced into the first zone directly, but can be introduced indirectly into the said zone; e.g. they can be introduced into the second zone and the liquid medium in the second zone can subsequently be transferred into the first zone (however, the basic agent is preferably not introduced into the second zone). These various constituents can be introduced separately or simultaneously. Once they have been introduced, chemical reactions, or at least equilibrated exchange reactions, can take place with the result that the exact nature of the constituents which are actually present in the liquid media, in particular in the first zone, is not necessarily that of the constituents in the form in which they were introduced.

As diphenols which are suitable for the process of the invention, there may be mentioned pyrocatechol, resorcinol and hydroquinone. However, pyrocatechol is preferred and it gives rise to ortho-alkenyloxyphenols.

$\beta,\gamma$-Unsaturated alkenyl halides which are preferably used are chlorides and bromides of the allyl type. Methallyl chloride is particularly suitable.

The organic solvent used is an inert solvent, i.e. a solvent which does not react chemically under the conditions of the process of the invention and is immiscible with water. Its b.p. is generally above 50° C. and preferably above 70° C. It is usually liquid at 20° C.

As solvents which can be used, there may be mentioned: aromatic hydrocarbons, such as e.g. toluene, o-, m- and p-xylenes, ethylbenzene and benzene, halogenohydrocarbons, such as e.g. 1,2-dichloroethane, trichloroethylene, perchloroethylene, methallyl chloride, chlorobenzene, o-, m- and p-dichlorobenzenes and trichlorobenzene, alcohols, such as e.g. n-amyl, n-hexyl, n-octyl and isoamyl alcohols and 2-ethylbutan-1-ol, ethers, such as e.g. dipropyl ether, dibutyl ether, dibenzyl ether, diisopropyl ether, diphenyl ether, anisole, phenetole and veratrole, ketones, such as e.g. 4-methylpentan-2-one, acetophenone and methyl isobutyl ketone, and nitriles, such as e.g. benzonitrile and propionitrile. The basic agent is advantageously a water-soluble inorganic compound. There may be mentioned alkali metal hydroxides (in particular sodium hydroxide, i.e. NaOH) or alkaline earth metal hydroxides, and alkali metal carbonates or bicarbonates, these compounds preferably being soluble in water.

The quaternary ammonium derivative is preferably a water-soluble salt or hydroxide. In general, the quaternary ammonium cation contains a total of between 10 and 40 carbon atoms.

As the quaternary ammonium derivative which can be used, there may preferably be mentioned those of the formula:

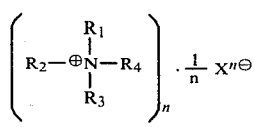

in which n is a positive integer equal to the valency of the anion X; $R_1$, $R_2$, $R_3$ and $R_4$, which are identical or different, each represent a hydrocarbon radical of which the chain is optionally interrupted by oxygen atoms (oxyalkylene or polyoxyalkylene chain), this radical being optionally substituted, in particular by hydroxyl groups; preferably, the radicals $R_1$, $R_2$, $R_3$ and $R_4$ have at most 30 carbon atoms; in particular, they can be of the alkyl, alkenyl (or hydroxyalkyl) or phenylalkyl type; and X is an inorganic or organic anion of valency n. As examples of anions which can be used, there may be mentioned chloride, bromide, fluoride, sulphate, bisulphate, $H_2PO_4^-$ and hydroxyl ions, alkoxysulphonyloxy ions (in particular those containing from 1 to 4 carbon atoms, such as methoxysulphonyloxy and ethoxysulphonyloxy ions), alkanesulphonyloxy ions (in particular those containing from 1 to 4 carbon atoms, such as methanesulphonyloxy or ethanesulphonyloxy ions), arylsulphonyloxy ions (in particular benzenesulphonyloxy or p-toluenesulphonyloxy ions) or alkanoyloxy ions containing from 1 to 4 carbon atoms (such as acetyloxy and propionyloxy ions).

The preferred quaternary ammonium derivatives are those of the alkyltributylammonium type in which the alkyl group possesses from 1 to 4 carbon atoms.

As the quaternary ammonium derivative, there may therefore be mentioned, more particularly, methyltributylammonium, ethyltributylammonium or tetrabutylammonium chlorides, hydroxides or bisulphates.

The phosphonium derivatives which can be used in the invention have the formula:

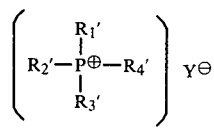

in which $R_1'$, $R_2'$, $R_3'$ and $R_4'$, which are identical or different, each represent an alkyl radical containing from 2 to 8 carbon atoms and Y represents a chlorine or bromine atom.

Especially in the case where pyrocatechol and methallyl chloride are employed, the temperature for the first zone is generally below 50° C. and preferably below 30° C. and the temperature for the second zone is above 50° C. and below 150° C. and preferably between 80° and 120° C. Depending on the temperature, it can of course be necessary to carry out the reaction in a container under pressure. The upper temperature limits are mainly related to the stability of the reagents employed. According to a preferred embodiment, the first zone is left at ambient temperature or at the natural temperature of the mixture, without any particular heating being carried out.

The concentration of the liquid media for the first zone and the second zone (i.e. the concentration of the total mixture of diphenol+alkenyl halide+basic agent-+ammonium or phosphonium derivative) is generally between 5 and 70% by weight and preferably between 30 and 60% by weight.

The concentration of ammonium or phosphonium derivative, relative to the organic solvent, is generally between 0.01 and 2 mols per liter of solvent and preferably between 0.1 and 1 mol/liter.

When both the basic agent and all or part of the liquid medium (preferably cooled), originating from the 2nd zone, are introduced into the first zone, either continuously or discontinuously (between 2 recycling operations), the respective amounts of these two additions are then such that the molar ratio $$\frac{\text{amount of basic agent introduced into the 1st zone}}{\text{amount of halide ions in the liquid transferred from the 2nd zone to the 1st zone}}$$

is less than or equal to 2 and preferably less than or equal to 1. The molar ratio $$\frac{\text{amount of basic agent introduced}}{\text{amount of diphenol introduced}}$$

is generally between 0.1 and 1 and preferably between 0.4 and 0.7. In a continuous operation, the amounts introduced which are shown in this ratio are instantaneous amounts or in other words molar flow rates. In a discontinuous operation, the total amount introduced from the start of the operation is taken into consideration.

The first zone is advantageously located in a mixer-decanter or in a liquid/liquid washing column operating in countercurrent.

The alkenyloxyphenols are useful as intermediates for the manufacture of aromas and perfumes. The orthoalkenyloxyphenols are useful as intermediates for the preparation of benzofurane derivatives having insecticidal properties.

The process of the invention is particularly valuable because of the good results obtained.

The following examples, which are given without implying a limitation, illustrate the invention and show how it can be put into practice.

EXAMPLE 1

Anisole (70 cc), degassed with argon, pyrocatechol (16.5 g), methallyl chloride (20 cc), tetrabutylammonium chloride (10 g) and an aqueous solution obtained using NaOH (1.49 g) and water (10 cc) are introduced, at 18° C., into a round-bottomed flask A equipped with a magnetic stirrer.

The temperature rises from 18° to 27° C. when the reagents are added.

The mixture is stirred for 20 minutes; it is left to separate out and the organic phase is then transferred into a round-bottomed flask B which is identical to A and has an argon atmosphere. The round-bottomed flask B is heated for 30 minutes at 100° C. and cooled to ambient temperature and its contents are reintroduced into the round-bottomed flask A.

A solution of sodium hydroxide (1.26 g) in water (5 cc) is added to the round-bottomed flask A and the same cycle of operations is repeated once; a solution of sodium hydroxide (1.29 g) in water (5 cc) is added to the round-bottomed flask A and the same cycle of operations is repeated twice without introducing further sodium hydroxide between these last two cycles of operations.

The contents of the round-bottomed flasks A and B are then combined and acidified to pH=4 (as regards the aqueous phase) with a N aqueous solution of sulphuric acid.

Extraction is carried out with ether and the ether extracts are washed with water.

This finally yields residual pyrocatechol (9.15 g), ortho-methallyloxyphenol (10 g) (yield of 91.3% relative to the pyrocatechol converted) and ortho-methallylpyrocatechol (0.08 g) (yield of 0.7% relative to the pyrocatechol converted).

EXAMPLE 2

Anisole (350 cc), methallyl chloride (100 cc), tetrabutylammonium chloride (50 g), pyrocatechol (45 g) and an aqueous solution (50 cc) containing sodium hydroxide (NaOH)(7.2 g) are introduced, at 18° C., into a round-bottomed flask A equipped with a magnetic stirrer.

The mixture is stirred for 20 minutes in the round-bottomed flask A and is then separated by decantation, and the organic phase is transferred into the round-bottomed flask B where it is heated for 30 minutes at 100° C.; the round-bottomed flask B is cooled to ambient temperature and its contents are reintroduced into the round-bottomed flask A.

Pyrocatechol (16.5 g) and a solution of sodium hydroxide (6 g) in water (25 cc) are added to this round-bottomed flask A and the same cycle of operations is repeated once; pyrocatechol (16.5 g) and a solution of sodium hydroxide (6 g) in water (25 cc) are added to the round-bottomed flask A and the same cycle of operations is repeated twice without introducing any further materials between these last two cycles of operations.

The following results are finally obtained: residual pyrocatechol (31.56 g) (degree of conversion 59.5%), ortho-methallyloxyphenol (61.5 g) (yield of 89% relative to the pyrocatechol converted) and ortho-methallylpyrocatechol (0.26 g) (yield of 0.4% relative to the pyrocatechol converted).

EXAMPLE 3

Anisole (70 cc), pyrocatechol (14.5 g), tetrabutylammonium chloride (10 g) and an aqueous solution (10 cc) containing sodium hydroxide (1.48 g) are introduced, at 18° C., into a round-bottomed flask A equipped with a magnetic stirrer.

After stirring for 20 minutes, the mixture is separated by decantation and the organic phase is transferred to the round-bottomed flask B; methallyl chloride (10 cc) is added to the latter round-bottomed flask B and the mixture is heated for 30 minutes at 100° C. After cooling, the contents of the round-bottomed flask B are reintroduced into the round-bottomed flask A and 3 similar cycles of operations are repeated successively.

The amount of sodium hydroxide introduced into the round-bottomed flask A before stirring, and the amount of methallyl chloride introduced into the round-bottomed flask B before heating, are indicated below for each cycle, it being understood that the 1st cycle repeats the operations which have just been described.

| No. of cycle | Sodium hydroxide in g | Methallyl chloride in cc |
|---|---|---|
| 1 | 1.48 | 10 |

-continued

| No. of cycle | Sodium hydroxide in g | Methallyl chloride in cc |
|---|---|---|
| 2 | 1.34 | 3.5 |
| 3 | 1.28 | 3.5 |
| 4 | 0 | 3.5 |

This finally yields residual pyrocatechol (5.73 g) (degree of conversion: 60.5%), ortho-methallyloxyphenol (11.9 g) (yield 91% relative to the pyrocatechol converted) and ortho-methallylpyrocatechol (0.08 g) (yield 0.6% relative to the pyrocatechol converted).

EXAMPLE 4

Anisole (70 cc), methallyl chloride (20 cc), tetrabutylammonium chloride (10 g), pyrocatechol (9 g) and an aqueous solution (10 cc) containing sodium hydroxide (1.5 g) are introduced, at 18° C., into a round-bottomed flask A equipped with a magnetic stirrer.

After stirring for 30 minutes at 25° C. and separating the mixture by decantation, the organic phase is transferred into a round-bottomed flask B which is heated for 1 hour 30 minutes at 90° C.

After cooling, pyrocatechol (3.27 g) is added and dissolved and the total mixture is reintroduced into the round-bottomed flask A to which a solution of sodium hydroxide (1.19 g) in water (5 cc) is also added. The cycle of operations already indicated is repeated twice, it being understood that pyrocatechol (3.38 g) is added to the round-bottomed flask B and sodium hydroxide (1.26 g) in water (5 cc) is added to the round-bottomed flask A between the last two cycles of operations.

This finally yields:

residual pyrocatechol: 6.67 g ortho-methallyloxyphenol: 12.11 g (yield 90.5% relative to the pyrocatechol converted).

We claim:

1. A process for the preparation of a $\beta,\gamma$-unsaturated alkenyloxyphenol from pyrocatechol and a $\beta,\gamma$-unsaturated alkenyl halide, wherein, in a first zone, there is a liquid medium consisting of two liquid phases of which one is organic and the other is aqueous, these phases being mixed with one another, and the liquid medium being obtained by mixing the pyrocatechol, the $\beta,\gamma$-unsaturated alkenyl halide, an organic solvent, a basic agent, water and a quaternary ammonium or phosphonium derivative, the temperature of this first zone being such that substantially no chemical reaction of the alkenyl halide takes place, and wherein the organic phase is then separated from the aqueous phase and is heated in a second zone, this heating being effected at a temperature which is sufficient for the alkenyl halide to react.

2. A process according to claim 1, wherein all or part of the liquid medium in the second zone is introduced into the first zone.

3. A process according to claim 2, wherein the liquid originating from the second zone is cooled before it is introduced into the first zone.

4. A process according to one of claims 2 or 3, wherein a further amount of the basic agent is added to the first zone.

5. A process according to one of claims 1 to 3, wherein the $\beta,\gamma$-unsaturated alkenyloxyphenol formed is extracted from the liquid medium in the second zone.

6. A process according to one of claims 1 to 3, wherein part of the organic phase is removed continuously from the second zone, this part is introduced into the first zone, part of the organic phase is extracted continuously from the first zone and this part is introduced into the second zone.

7. A process according to claim 6, wheren the basic agent is introduced continuously into the first zone.

8. A process according to one of claims 1 to 3, wherein the alkenyl halide is methallyl chloride.

9. A process according to claim 1, wherein the temperature of the first zone is below 50° C. and the temperature of the second zone is above 50° C. and below 150° C.

10. A process according to one of claims 1 to 3, wherein the organic solvent is immiscible with water, has a b.p. above 50° C., is liquid at 20° C. and is an aromatic hydrocarbon, a halogenohydrocarbon, an alcohol, an ether, a ketone or a nitrile.

11. A process according to one of claims 1 to 3, wherein the basic agent is an alkali metal hydroxide or carbonate.

12. A process according to one of claims 1 to 3, wherein the quaternary ammonium derivative is a water-soluble hydroxide or salt, the cationic part of which contains between 10 and 40 carbon atoms.

13. A process according to one of claims 1 to 3, wherein the concentration of the liquid media for the 1st and the 2nd zone is between 5 and 70% and the concentration of ammonium or phosphonium derivative, relative to the organic solvent, is between 0.01 and 2 mols/liter.

14. A process according to claim 13, wherein the concentration of the liquid media is between 30 and 60% or the concentration of ammonium or phosphonium derivative is between 0.1 and 1 mol/liter.

15. A process according to one of claims 1 to 3, wherein the molar ratio $$\frac{\text{amount of basic agent introduced}}{\text{amount of pyrocatechol introduced}}$$

is between 0.1 and 1.

16. A process according to claim 15, wherein this ratio is between 0.4 and 0.7.

17. A process according to claim 8, wherein the temperature of the first zone is below 30° C. and the temperature of the second zone is between 80° and 120° C.

18. A process according to claim 4, wherein the $\beta,\gamma$-unsaturated alkenyloxyphenol formed is extracted from the liquid medium in the second zone.

19. A process according to claim 18, wherein part of the organic phase is removed continuously from the second zone, this part is introduced into the first zone, part of the organic phase is extracted continuously from the first zone and this part is introduced into the second zone.

20. A process according to claim 19, wherein the organic solvent is immiscible with water, has a b.p. above 50° C., is liquid at 20° C. and is an aromatic hydrocarbon, a halogenohydrocarbon, an alcohol, an ether, a ketone or a nitrile.

21. A process according to claim 20, wherein the basic agent is an alkali metal hydroxide or carbonate.

22. A process according to claim 21, wherein the quaternary ammonium derivative is a water-soluble hydroxide or salt, the cationic part of which contains between 10 and 40 carbon atoms.

23. A process according to claim 22, wherein the concentration of the liquid media for the first and second zone is between 5 and 70% and the concentration of ammonium or phosphonium derivative, relative to the organic solvent, is between 0.01 and 2 mols/liter.

24. A process according to claim 23, wherein the molar ratio $$\frac{\text{amount of basic agent introduced}}{\text{amount of pyrocatechol introduced}}$$

is between 0.1 and 1.

25. A process according to claim 24, wherein the molar ratio $$\frac{\text{amount of basic agent introduced}}{\text{amount of pyrocatechol introduced}}$$

is between 0.4 and 0.7.

26. A process according to claim 4, wherein a further amount of the pyrocatechol is added to the first zone or to the second zone.

27. A process according to claim 4, wherein a further amount of the $\beta,\gamma$-unsaturated alkenyl halide is added to the first zone or to the second zone.

* * * * *